US008057659B2

(12) United States Patent
Harding et al.

(10) Patent No.: US 8,057,659 B2
(45) Date of Patent: Nov. 15, 2011

(54) DETECTION OF ANALYTES IN A DUAL-MEDIATOR ELECTROCHEMICAL TEST STRIP

(75) Inventors: Ian Harding, Somerville, MA (US); Sridhar Iyengar, Salem, NH (US)

(73) Assignee: AgaMatrix, Inc., Salem, NH (US)

(*) Notice: Subject to any disclaimer, the term of this patent is extended or adjusted under 35 U.S.C. 154(b) by 253 days.

(21) Appl. No.: 11/768,341

(22) Filed: Jun. 26, 2007

(65) Prior Publication Data

US 2007/0295616 A1 Dec. 27, 2007

Related U.S. Application Data

(60) Provisional application No. 60/805,918, filed on Jun. 27, 2006.

(51) Int. Cl.
*G01N 27/327* (2006.01)

(52) U.S. Cl. .............. 205/792; 204/403.14; 204/403.11; 435/14; 435/4; 435/25; 205/777.5

(58) Field of Classification Search .............. 205/777.5, 205/779, 775, 778, 792; 204/403.01–403.15, 204/400; 435/4, 14, 25
See application file for complete search history.

(56) References Cited

U.S. PATENT DOCUMENTS

| 5,120,420 | A |   | 6/1992 | Nankai et al. | |
|---|---|---|---|---|---|
| 5,352,351 | A | * | 10/1994 | White et al. | 204/403.04 |
| 5,393,903 | A |   | 2/1995 | Gratzel et al. | |
| 5,437,999 | A | * | 8/1995 | Diebold et al. | 204/403.11 |
| 5,508,171 | A |   | 4/1996 | Walling et al. | |
| 5,589,326 | A | * | 12/1996 | Deng et al. | 435/4 |
| 5,846,702 | A |   | 12/1998 | Deng et al. | |
| 5,958,199 | A |   | 9/1999 | Miyamoto et al. | |
| 6,033,866 | A | * | 3/2000 | Guo et al. | 435/14 |
| 6,262,264 | B1 |   | 7/2001 | Buck, Jr. et al. | |
| 6,287,451 | B1 |   | 9/2001 | Winarta et al. | |
| 6,338,790 | B1 |   | 1/2002 | Feldman et al. | |
| 6,352,824 | B1 |   | 3/2002 | Buck, Jr. et al. | |
| 6,576,101 | B1 |   | 6/2003 | Heller et al. | |
| 6,605,201 | B1 |   | 8/2003 | Mao et al. | |
| 6,676,816 | B2 |   | 1/2004 | Mao et al. | |
| 7,074,308 | B2 |   | 7/2006 | Mao et al. | |
| 7,090,756 | B2 |   | 8/2006 | Mao et al. | |
| 7,615,637 | B2 |   | 11/2009 | Mao et al. | |
| 7,807,835 | B2 |   | 10/2010 | Xie et al. | |
| 2003/0175841 | A1 | * | 9/2003 | Watanabe et al. | 435/14 |
| 2005/0084921 | A1 | * | 4/2005 | Cranley et al. | 435/25 |

(Continued)

OTHER PUBLICATIONS

Dermont Diamond, Principles of Chemical and Biological Sensors, 1998, p. 116.*

(Continued)

*Primary Examiner* — Jeffrey T Barton
*Assistant Examiner* — Jennifer Dieterle
(74) *Attorney, Agent, or Firm* — Larson & Anderson, LLC

(57) ABSTRACT

Determination of an analyte such as glucose in a sample is done making use of a plurality of electron transfer reagents, for example two electron transfer reagents, that work together to transfer electrons between the enzyme and the electrodes. The first electron transfer agent is a mediator that interacts with the enzyme after it has acted on the analyte to regenerate enzyme in its active form. The second electron transfer agent is a shuttle that interacts with the electrodes and optionally the mediator. The oxidation and reduction of the shuttle serves as the major source of current that is measured as an indication of analyte.

9 Claims, 5 Drawing Sheets

U.S. PATENT DOCUMENTS

2005/0109637 A1     5/2005    Iyengar et al.
2005/0258035 A1    11/2005    Harding et al.
2006/0025593 A1     2/2006    Xie et al.
2006/0231423 A1    10/2006    Harding et al.

OTHER PUBLICATIONS

Healy et al, Biochemistry, vol. 12, No. 1, 1973, pp. 35-41.*
Basu, Dept. of Chemistry, University College of Science, 92 Upper Circular Road, Calcutta-9, India Received Apr. 27, 1955, pp. 7-9.*
Hamann et al., J.Am. Chem. Soc. 2005, 127, pp. 13949-13954.*
Wang, Joseph, "Glucose biosensors: 40 years of advances and challenges", In: Electroanalysis; Aug. 9, 2001, pp. 983-988; vol. 13(12).
Zie, Hong et al., "Electrochemical activation of glucose oxidase with a 140-fold enhancement in intramolecular electron transfer rate constant"; In: Frontiers in Bioscience; Sep. 1, 2005; pp. 2770-2775; vol. 10.
Nakabayashi et al., Evaluation of Osmium(II) Complexes as Electron Transfer Mediators Accessible for Amperometric Glucose Sensors, Analytical Sciences, Aug. 2001, pp. 945-950, vol. 17, The Japan Society for Analytical Chemistry.
Nakabayashi et al., Evaluation of osmium(II) complexes as mediators accessible for biosensors, Sensors and Actuators B 66, 2000, pp. 128-130, Elsevier Science S.A.
Warren, Susan et al. "Investigation of novel mediators for a glucose biosensor based on metal picolinate complexes" 2005, pp. 23-35, vol. 67, Bioelectrochemistry.

* cited by examiner

Legend:
Filled square (■) – Ferricyanide + Osmium
Empty Circle (○) – Ferricyanide only

DETECTION OF ANALYTES IN A DUAL-MEDIATOR ELECTROCHEMICAL TEST STRIP

This application claims the benefit of U.S. Provisional Application Ser. No. 60/805,918, filed Jun. 27, 2007, which is incorporated herein by reference in its entirety.

BACKGROUND OF THE INVENTION

This application relates to the electrochemical detection of analytes in a test sample. The invention is particularly applicable to the detection of glucose in a sample of blood or other biological fluid using a disposable electrochemical test strip. FIG. 1 shows a schematic representation of a conventional enzyme biosensor for the electrochemical detection of glucose. The biosensor has a working electrode 10 and counter electrode 11 in a circuit with a voltage source 12. The sample is disposed between the electrodes 10,11 to complete the circuit. When glucose is present, glucose oxidase, GOXox present in the sensor oxidizes the glucose to gluconolactone and reduced enzyme, GOXred is formed. An oxidized mediator, MEDox, present in the sensor restores the enzyme to the active oxidized form, GOXox, and generates reduced mediator, MEDred. The applied voltage in the circuit is selected such that reduced mediator is oxidized at electrode 11 and that oxidized mediator, MEDox, is reduced at electrode 10. Current flow within the sensor results from the oxidation and reduction of the mediator at the electrodes, and this current flow is frequently measured to assess the amount of glucose in the sample. The biosensor shown in FIG. 1 can be modified for use with other analytes, for example by selection of a redox enzyme (oxidase, dehydrogenase etc.) with different specificity appropriate for the other analyte.

Numerous mediators have been disclosed for use in biosensors of the type shown in FIG. 1. In general, suitable mediators are ferricyanide, metallocene compounds such as ferrocene, quinones, phenazinium salts, redox indicator DCPIP, and bipyridyl-substituted osmium compounds. See, for example, U.S. Pat. Nos. 5,589,32, 6,338,790 which are incorporated herein by reference. In selecting a mediator to use with a particular analyte, several factors are generally relevant. For example, in the case of glucose, the mediator is selected to have a redox potential that allows it to regenerate the enzyme, glucose oxidase, from the reduced to the oxidized state. In addition, if the kinetics of the reaction with the enzyme are slow, the reduced enzyme may also react with oxygen present in this sample, leading to errors as a result in differences in hematocrit and blood $pO_2$. (FIG. 2) Thus, it is also desirable to have fast kinetics for the enzyme-mediator reaction. It is frequently the case, however, that compounds that meet the desired criteria for redox potential and kinetics are poorly soluble in aqueous solutions, such as blood. This means that the maximum concentration of mediator is limited, and as a result that the maximum amount of signal that can be generated is limited.

SUMMARY OF THE INVENTION

The present invention provides for improved determination of an analyte such as glucose in a sample by making use of a plurality of electron transfer reagents, for example two electron transfer reagents, that work together to transfer electrons between the enzyme and the electrodes. A first electron transfer agent is a mediator that interacts with the enzyme after it has acted on the analyte to regenerate enzyme in its active form. The second electron transfer agent is a shuttle that interacts with the electrodes and optionally the mediator. The oxidation and reduction of the shuttle serves as the major source of current.

DETAILED DESCRIPTION OF THE INVENTION

Figure 1:
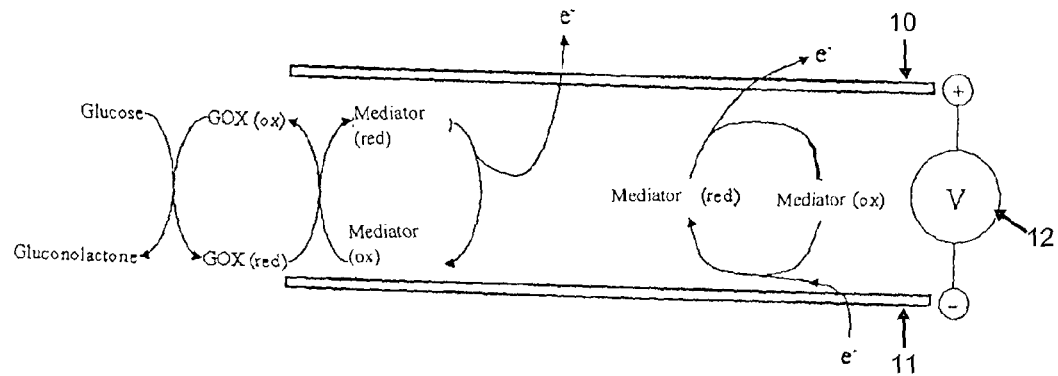
FIG. 1 shows a schematic representation of an enzyme biosensor in accordance with the prior art.

In the present application and claims, the following definitions are applicable:

"analyte" refers to the material of interest in a sample. The analyte may be, for example, a chemical of biological significance such as glucose, lactate, cholesterol, fructose, alcohol, amino acids, creatine and creatinine.

"detection of analyte in a sample" refers to the qualitative, semi-quantitative or quantitative determination of whether an analyte is present in a sample at detectable levels. Qualitative analysis provides merely a yes/no answer as to whether there is detection. Semi-quantitative provides an indication of amount, but with high granularity, for example as presented through a series of lights where the number of lights illuminated indicates the range into which a value falls. Quantitative analysis provides a numerical value for the amount of analyte in the measured sample.

"electron transfer reagent" refers to a compound other than a redox enzyme that receives and donates electrons to and/or from another chemical species or to and/or from an electrode. The mediator compound and the shuttle compound of the present invention are both electron transfer reagents.

"mediator compound" refers to an electron transfer reagent that in use reacts with the inactive enzyme to regenerate active enzyme. The mediator compound may also transfer electrons to or from the electrodes although this is not required. In some embodiments, the mediator compound does not transfer electrons directly to or from the shuttle compound. In other embodiments, electron transfer between mediator and shuttle in solution can happen and in other embodiments electron transfer between mediator and shuttle is the most significant method of transferring electrons from the mediator "redox enzyme" refers to an enzyme that catalyzes oxidation or reduction of the analyte to be determined. Exemplary redox enzymes are oxidases such as glucose oxidase and dehydrogenases such as glucose dehydrogenase or lactate dehydrogenase. The redox enzyme has an active form prior to interaction with the analyte, and an inactive form. In the case of an oxidase, for example, the active form is oxidized and the inactive form is reduced.

"sample" refers to the material that is placed in the sample chamber to perform a determination for analyte. The sample is applied as a liquid, although samples that are not liquid in the first instance can be combined with a liquid to produce a sample for application. In general, the sample is a biological fluid such as blood, serum, urine, saliva or sputum.

"shuttle compound" refers to an electron transfer reagent that in use transfers electrons to and from the electrodes. In some embodiments of the invention, the shuttle is reduced by transfer of an electron from one electrode and oxidized by transfer of an electron to the other electrode. In other embodiments, the shuttle also can be reduced (or oxidized) by transfer of an electron from the reduced mediator (or to the oxidized mediator). In this instance, in one preferred embodiment, the mediator itself does not react at the electrodes.

Theory of the Invention

The present invention utilizes a dual system of a mediator and a shuttle compound to separate the characteristics of an "ideal" mediator into two entities, where the overall result can come closer to ideality. The mediator in the present invention has an appropriate $E^o$ value based on the redox potential of the enzyme to be regenerated. In the case of glucose oxidase, this is a value of less than 150 mV. For other enzymes, the value may vary somewhat. Second, the mediator has a fast rate of transfer from the enzyme or an enzyme-coenzyme complex. "Fast" refers to the rate of transfer relative to the rate of reaction of the reduced enzyme with oxygen. This rate is dependent on the specific enzyme. However, in general, it is desirable to have the rate of electron transfer to the mediator be at least 10 times the rate of electron transfer to oxygen, preferably at least 100 times, and even more preferably at least 1000 times.

The shuttle compound used in the present invention is selected such that it has slow or no reaction with oxygen. This reaction with oxygen is based on the presence of at most minimal reaction with oxygen during the duration of the test. Slow means that there is some observable reaction of reduced shuttle with oxygen in this time period, but that the amount does not change the measured signal by more than 10%. No reaction means that there is no detectable oxygen-dependent variation in signal over the duration of the test.

The shuttle compound is also "highly soluble." In this context, the term "highly soluble" refers to solubility relative to the mediator employed in the sensor. This allows the concentration of shuttle to be in excess over the concentration of the mediator, for example more than 10 times the mediator concentration, preferably more than 50 times the mediator concentration, and more preferably more than 100 times the mediator concentration.

Figure 3:
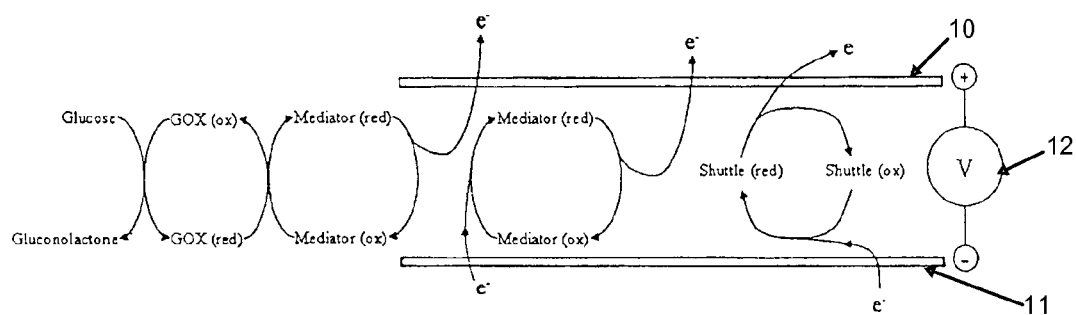
FIG. 3 shows a schematic representation of an enzyme biosensor in accordance with an embodiment of the invention.

FIG. 3 shows the co-operation of the mediator and shuttle in accordance with one embodiment of the invention. In this embodiment of the invention, mediator interacts with the enzyme glucose oxidase and is oxidized/reduced at the electrodes 10, 11 in a conventional manner. The shuttle compound is also oxidized/reduced at the electrodes 10, 11, but there is no direct interaction between the mediator and the shuttle. Faradaic reaction of the shuttle is initiated by the passing of an electron from the reduced mediator to the positive electrode 12, and the completion of the circuit by shuttle (ox) accepting an electron from the negative electrode 11. Faradaic reaction of the mediator may also occur and the observed current is no different when it does. However, the greater concentration of the shuttle will make this a lesser component of the current.

Figure 4:
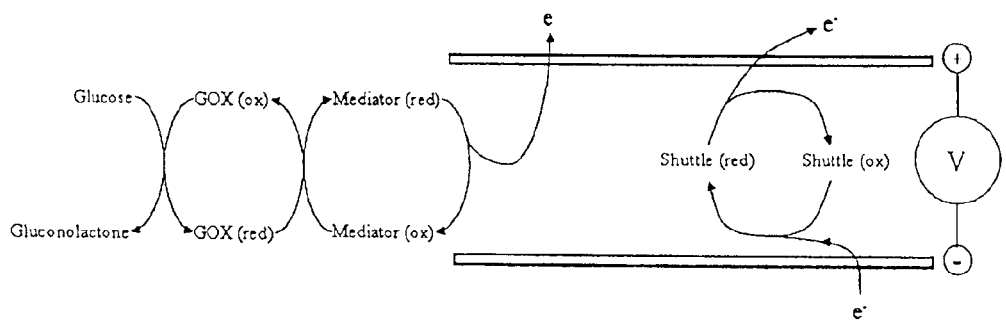
FIG. 4 shows a schematic representation of an enzyme biosensor in accordance with an embodiment of the invention.

FIG. 4 shows a schematic representation of a dual mediator sensor in accordance with another embodiment of the invention. The sensor depicted in FIG. 4 is similar to the sensor of FIG. 3 except that in this case there is no Faradaic reaction of the mediator at the negative electrode 11.

Figure 2:
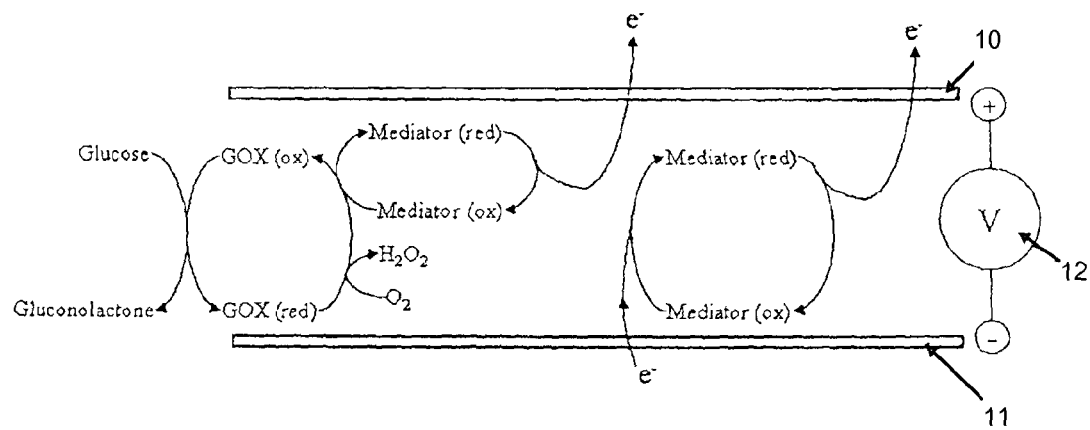
FIG. 2 shows a schematic representation of an enzyme biosensor in accordance with the prior art with oxygen reaction with reduced enzyme in competition with the mediator.

The dual-mediator sensors as depicted in FIGS. 1 and 2 offer several advantages over conventional sensors because of the separation of characteristics. These may include:

(1) The applied potential required to turn over the mediator (<150 mV) does not drive other redox reactions.

(2) The mediator can be chosen such that it has a fast rate of electron transfer from the reduced enzyme, thereby limiting the loss of signal due to oxygen reacting with the reduced enzyme, without worrying about also solving the solubility issues.

(3) The shuttle reacts slowly, or not at all, with O2, so there is minimal or no loss of signal caused by oxidation of the reduced shuttle by O2.

(4) Contrary to the mediator, which is often limited to a low concentration by solubility or economic reasons, the shuttle is highly soluble, so that Faradaic reaction of the shuttle is not limited by availability of the molecule in solution.

(5) The shuttle has a fast rate of Faradaic reaction.

(6) The shuttle is inexpensive, so it is included in great excess over the mediator, ensuring that a counter reaction is available and that the constant current due to Faradaic reaction of the shuttle is maintained.

Figure 5:
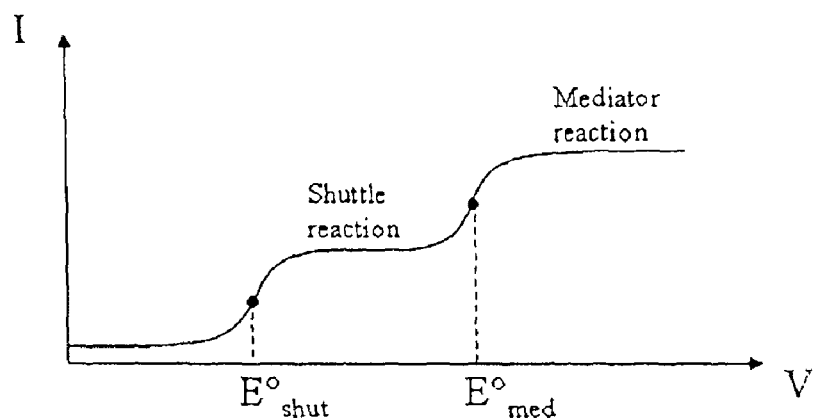
FIG. 5 shows a possible relationship between $E^0$ values for the shuttle and mediator.

As is apparent from consideration of FIGS. 3 and 4, the potential required to oxidize/reduce the mediator and shuttle may be different. This difference can be tuned through the selection of the mediator and shuttle to provide for the desired form of operation in the sensor. FIG. 5 illustrates the case where the $E^0$ of the mediator is greater than the $E^0$ of the shuttle, i.e. $E^o_{med} > E^o_{shut}$. The following observations can be made with respect to this situation. If $V_{app}$ (the applied potential) $> E^o_{med}$, then both the mediator reaction and the shuttle reaction proceed and measurements can be taken as per usual. If $E^o_{shut} < V_{app} < E^o_{med}$, the shuttle reaction proceeds, but the mediator reaction does not, i.e. all of the mediator in solution is trapped in the reduced state.

Since all of the mediator is trapped in the reduced state, the enzyme reaction can be stopped, (assuming there is no oxygen to turn over the enzyme) by controlling the potential. This is a unique advantage since we can then selectively stop the enzyme reaction as some particular point in time before proceeding with a measurement. Non-limiting examples of when this might be useful are:

(1) If the sensor's ambient temperature falls outside a range and it is desirable to wait until the conditions become suitable for a measurement (2) If there is excessive ambient noise (e.g. RF, vibration, etc) and it is desirable to wait until the noise subsides before making a measurement.

(3) If there is insufficient sample in the test strip and it is desirable to wait until the chamber is fully filled before continuing with a measurement.

Figure 6:
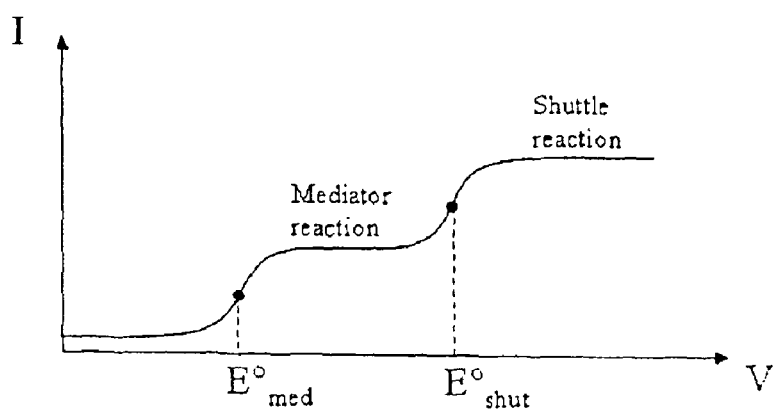
FIG. 6 shows another possible relationship between $E^0$ values for the shuttle and mediator.

FIG. 6 shows an alternative selection of mediator and shuttle in which $E^0_{shut} > E^0_{med}$. In this case, $V_{app}$ (the applied potential) must be greater than $E^o_{shut}$ in order to ensure that both the mediator reaction and the shuttle reaction proceed. It is advantageous to have $E^o_{shut} < 150$ mV, so that the applied potential required to turn over all reactions does not drive other redox reactions. This is important, since the blood contains several other redox active species (e.g., ascorbate, proteins, metabolites, etc.), which may contribute to the electrochemical current, resulting in spurious blood glucose readings.

Figure 7:
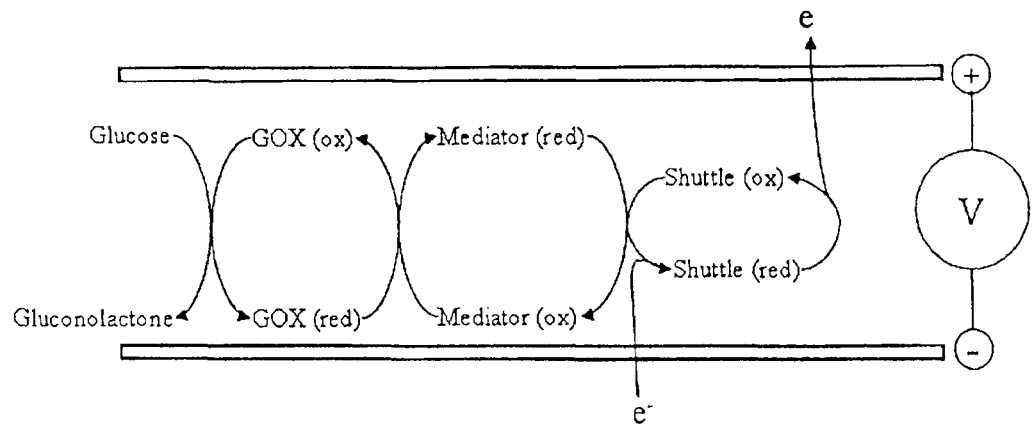
FIG. 7 shows a schematic representation of an enzyme biosensor in accordance with an embodiment of the invention.
Figure 8:
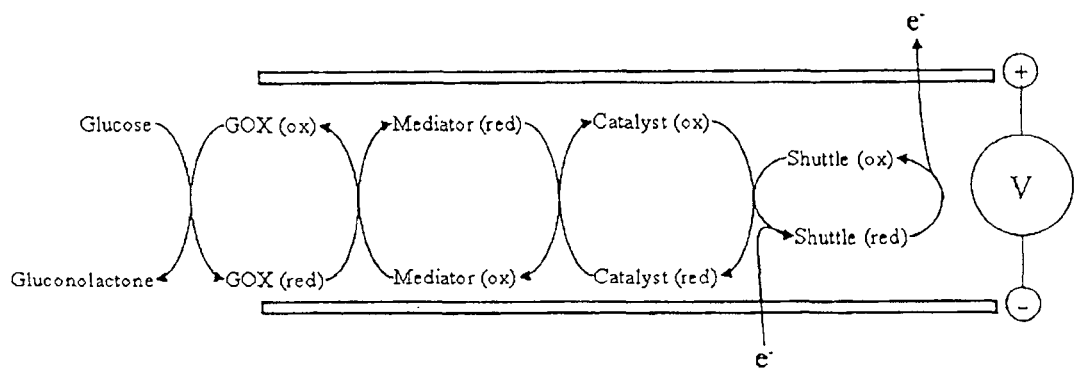
FIG. 8 shows a schematic representation of an enzyme biosensor in accordance with an embodiment of the invention.

FIG. 7 shows a schematic representation of a further embodiment of the invention. In this embodiment, there is direct reaction between the mediator and the shuttle, and the mediator does not significantly undergo Faradaic reaction at the electrode. FIG. 8 shows a similar embodiment in which the reaction of the mediator with the shuttle is coupled through a redox catalyst. This redox catalyst is a third electron transfer agent.

In the foregoing discussion, the $E^0$ of the mediator is referred to. It should be appreciated, however, that specific knowledge of absolute $E^0$ values is not required, and that what is important is the relative values for the materials being utilized as mediator and shuttle. This can easily be obtained experimentally at the conditions found in the test strip (pH, temperature etc) without requiring the more detailed measurements to determine an $E^0$ value under standardized conditions.

Sensor of the Invention

According to one aspect, the present invention provides a sensor for the detection of an analyte in a sample. The sensor of the present invention comprises:

(a) a support portion defining a sample chamber;

(b) a working and a counter electrode disposed within the sample chamber; and (c) a reagent composition disposed in the sample chamber, said reagent composition comprising (i) an active redox enzyme effective to oxidize or reduce the analyte, (ii) a mediator compound, and (iii) a shuttle compound. In certain preferred embodiments, the sensor is intended for single use, and is used in combination with a reusable device or meter that provides the analysis electronics and display or other communications means to convey a test result to the user. The sensor may, however, be part of an integrated device that includes both the recited elements and the electronics and display/communications means.

Sensors for use in the detection of glucose and other analyte species are known, and the structures of these sensors are representative of and useable as the support portion and the electrodes of the sensor of the present invention. Specific non-limiting examples of support and electrode configurations are found in U.S. Pat. Nos. 5,120,420, 5,437,999, 5,958, 199, 6,287,451, and 6,576,101 and US Patent Publication No. 2005-0258035, which are incorporated herein by reference.

The reagent composition disposed in the sample chamber contains an active redox enzyme effective to oxidize or reduce the analyte. As will be apparent, the specific enzyme is selected based on its specificity for the analyte. Non-limiting examples of suitable enzymes include glucose oxidase, fructose dehydrogenase, glucose dehydrogenase, alcohol oxidase, lactate oxidase, cholesterol oxidase, xanthine oxidase, and amino acid oxidases.

The general characteristics of compounds useful as mediators in the compositions of the invention are set forth above. Specific, non-limiting examples of suitable mediators include osmium-containing mediators such as $[Os(MeBpy)_2(Im)_2]^{2+/3+}$. The solubility of the $PF_6$ salt of this complex is less than 1 mM and it has a redox potential $E^0=140\text{-}154$ mV. The second order rate constant of electron transfer from GOX to the 3+ mediator is approximately $4.0\times10^5$ $M^{-1}s^{-1}$. Another specific mediator is $[Os(Mebpy)2Pic]^{+/2+}$. Other examples of good mediators (which may not have good solubility) are: Ferrocenes and other metallocenes in general, with various derivatizations (especially sulfonation); Metal compounds (especially, but not limited to, Ru, Os, Fe, and Co) containing ligands of the following types, which may be derivatized with substituent groups to enhance solubility, tune redox potential and ligating abilities, or for other reasons: bipyridyl, phenanthroline, imidazole, thiolene/thiolate/thioether/sulfide, porphyrins, pyrrole/pyrrazole/thiazole/diazole/triazole, picolinate, carboxylate, oxo, quinone; Metal clusters (i.e. more than one metal in the compound).

Non-limiting examples of suitable shuttles include:

Metal complexes (especially, but not limited to, Ru, Os, Fe, and Co) of monodentate ligands, including, but not limited to: hydrates/hydroxo, aminates, acetates, thiolates, halides, thiocyanates, cyanides, especially ferricyanide;

Metal complexes (especially, but not limited to, Ru, Os, Fe, and Co) of multidentate ligands (which may be derivatized to enhance solubility, tune redox potential and ligating abilities, or for other reasons), including, but not limited to: Aminoacetates, EDTA (Ethylenediaminetetraacetic acid), especially Fe(III)-EDTA, Ru(III)-EDTA and CO(III)-EDTA, HEDTra (hydroxyethylethylenediamine triacetic acid), NTA (Nitrilotriacetic acid), ADA (β-alaninediacetic acid), MGDA (methyleneglycine diacetic acid), IDS (iminodisuccinate), GLUDA (glutamate N,N'-bisdiacetic acid), EDDS (ethylenediamine disuccinic acid) DTPA (Diethylenetriaminepentaacetic acid);

Polyethers, for example cryptates and/or encapsulating ligands and crown ethers

Polycarboxylates such as citrates, oxalates, tartrates, succinates, and malonates;

Phosphonates;

Polyamines with a varied number and identity of ligands in the chain.

Tetradentate:

2,3,2-triethylenetetramine
[$N_{H2}CH_2CH_2NHCH_2CH_2CH_2NHCH_2CH_2NH_2$]

3,2,3-triethylenetetramine
[$NH_2CH_2CH_2CH_2NHCH_2CH_2NHCH_2CH_2CH_2NH_2$]

3,3,3-triethylenetetramine
[$NH_2CH_2CH_2CH_2NHCH_2CH_2CH_2NHCH_2CH_2CH_2NH_2$]

NSSN-Type Ligands:
$NH_2CH_2CH_2SCH_2CH_2SCH_2CH_2NH_2$
$NH_2CH_2CH_2SCH_2CH_2SCH_2CH_2NH_2$
$NH_2CH_2CH_2SCH_2CH_2CH_2SCH_2CH_2NH_2$
$NH_2CH_2CH_2CH_2SCH_2CH_2SCH_2CH_2CH_2NH_2$ SNNS-Type Ligands:
$HSCH_2CH_2N(CH_3)CH_2CH_2N(CH_3)CH_2CH_2SH$
$HSCH_2CH_2N(CH_3)CH(CH_3)CH_2N(CH_3)CH_2CH_2SH$
$HSCH_2CH_2N(CH_3)CH_2CH_2CH_2N(CH_3)CH_2CH_2SH$
$HSC(CH_3)2CH_2NHCH_2CH_2NHCH_2C(CH_3)2CSH$ Pentadentate:
$NH_2CH_2CH_2SCH_2CH_2N(CH_3)CH_2CH_2SCH_2CH_2NH_2$
$NH_2CH_2CH_2SCH_2CH_2SCH_2CH_2SCH_2CH_2NH_2$.

Method of the Invention

The present invention also provides a method in which the sensor described above is used in for detecting an analyte. In accordance with this method, the sample is applied to the sensor. A potential is applied between the working and counter electrodes, and the current between the electrodes is observed. An indication of the presence or absence of detectable amounts of analyte in the sample is generated based on the observed current. As will be appreciated by persons skilled in the art, this method is advantageously practices using a meter that contains the electronics for applying the potential, observing the current, and generating a determination of analyte and conveying it to the user. Numerous meters for this purpose have been disclosed, and the particular design of the meter is not critical.

In accordance with a first embodiment of the method of the invention, the voltage difference applied to electrodes. $V_{app}$, is greater than both $E^0_{shut}$ and $E^0_{med}$ such that both the shuttle and the mediator can react at the electrodes as depicted in FIG. 3.

In accordance with a second embodiment of the method of the invention, $E^0_{shut}$ is less than $E^0_{med}$ and the voltage difference applied to electrodes, $V_{app}$, is intermediate between $E^0_{shut}$ and $E^0_{med}$ such that only the shuttle reacts at the electrodes as depicted in FIG. 7.

EXAMPLE 1

Calibration curves were prepared to compare the performance of a reagent formulae that had ferricyanide alone as the mediator, and one in accordance with the invention that use ferricyanide as a shuttle and the poorly soluble $PF_6$ salt of $[Os(MeBpy)_2(Im)_2]^{2+/3+}$ as a mediator for the reaction of glucose and glucose oxidase. In each case, the amount of glucose oxidase was the same, and the applied voltage was 150 mV. The two reagent formulations were as follows:
1. Ferricyanide alone, as both shuttle and mediator: reagent: 100 mM ferri, 5 mM phosphate buffer pH 8.1, +stabilizers, sample: 200 mM citrate buffer pH 4.1, 133 nK NaCl
2. Ferricyanide (as a shuttle)+Osmium salt (as efficient mediator): reagent: saturated (<1 mM) Osmium salt, 100 mM ferri, 5 mM phosphate buffer pH 8.1, and stabilizers, sample 50 mM phosphate buffer pH 8.1, 133 mM NaCl.

In each case, the stabilizers were polyethyleneglycol and erythritol. Sample pH is different in each case. -The chosen pH represents the optimal pH for that mediator system. One would not expect Ferricyanide (which is optimized at pH 4.1) to mediate well at pH 8.1, whereas it is ideal for Osmium, and the difference in pH was therefore adopted to confirm that better performance was in fact being achieved and that the observed difference was not an artifact.

Figure 9:
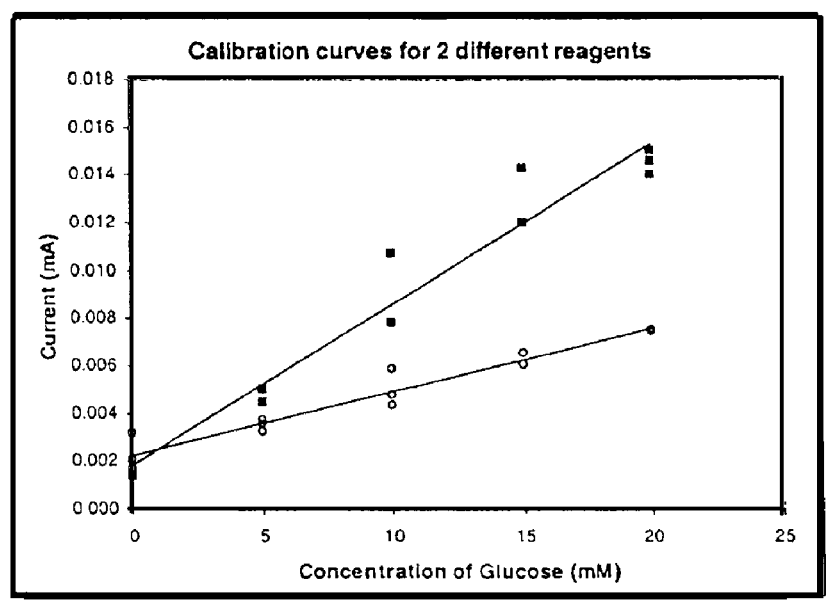
FIG. 9 shows experimental results using a dual mediator system of the invention as compared to a single mediator system.

FIG. 9 shows the observed calibration curves (current versus glucose concentration) for the two reagents. When ferricyanide is used alone, it has to function as a mediator and a shuttle and is therefore inefficient resulting in lower currents at any given concentration. When used in combination, ferricyanide (high solubility, slow electron transfer rate from enzyme) and osmium (low solubility, fast rate of electron transfer from the reduced enzyme) function as an efficient shuttle and mediator respectively, resulting in higher observed currents and a greater slope. Higher observed currents and the greater slope allows for improved accuracy and greater dynamic range.

EXAMPLE 2

A reagent formulation was prepared as follows:
100 mM phosphate buffer (pH 7.0), 100 mM ferricyanide, 50 mN alanine anhydride, 1 mM Os(Mebpy)$_2$PicCl (~1 mg/ml), 2.6 mg/ml Surfactant 10 G (Arch Chemicals).
Good results measuring glucose were obtained using this formulation.

EXAMPLE 3

A reagent formulation was prepared as follows:
100 mM phosphate buffer (pH 7.0), 100 mM ferricyanide, 50 mN alanine anhydride, saturated (<1 mM) [Os(Mebpy)$_2$Im$_2$](PF$_6$)$_2$, 2.6 mg/ml Surfactant 10 G (Arch Chemicals), 1% w/v silica (AERODISP W7520N, Degussa).
Good results measuring glucose were obtained using this formulation.
In the formulas above, MeBpy=4.4' dimethyl-2,2'-bipyridyl, Pic=Picolinate, the conjugate base of Picolinic Acid. Alanine Anhydride is a stabilizer (See U.S. Pat. No. 3,243, 356) and silica is a stabilizer (See, U.S. Pat. No. 3,556,945).

What is claimed is:
1. A method for detecting glucose in a sample comprising the steps of:
 (a) applying a sample to be evaluated for the presence of glucose to a test strip, wherein the test strip comprises:
  a support portion defining a sample chamber;
  a working and a counter electrode disposed within the sample chamber; and
  a reagent composition disposed in the sample chamber, said reagent composition comprising (i) an active redox enzyme effective to oxidize glucose in the sample, (ii) a mediator compound, and (iii) a shuttle compound, wherein the shuttle compound and the mediator compound are different from one another; wherein
  when a sample containing analyte is introduced into the sample chamber, the redox enzyme oxidizes glucose the analyte and produces an inactive enzyme that is reduced,
  the mediator is [Os(Mebpy)$_2$Pic]$^{+/2+}$ and
  the shuttle is ferri/ferrocyanide, and
 (b) applying a potential between the working and the counter electrodes to generate current that is indicative of the amount of glucose in the sample.
2. A method for detecting an analyte in a sample comprising the steps of:
 introducing the sample into a sensor, wherein said sensor comprises:
 (a) a support portion defining a sample chamber;
 (b) a working and a counter electrode disposed within the sample chamber; and
 (c) a reagent composition disposed in the sample chamber, said reagent composition comprising (i) an active redox enzyme effective to oxidize the analyte, (ii) a mediator compound, and (iii) a shuttle compound, wherein
  when a sample containing analyte is introduced into the sample chamber, the redox enzyme oxidizes the analyte and produces an inactive enzyme that is reduced,
  the mediator is [Os(Mebpy)$_2$Pic]$^{+/2+}$ and
  the shuttle is ferri/ferrocyanide.
3. The method of claim 2, wherein the shuttle compound is present in at least a ten-fold excess with respect to the mediator compound on a molar basis.
4. The method of claim 2, wherein the reagent composition further comprises a third electron transfer agent that transfers electrons between the mediator and the shuttle.
5. The method of claim 2, wherein the analyte is glucose and the enzyme is glucose oxidase.
6. A sensor for the detection of an analyte in a sample, comprising:
 (a) a support portion defining a sample chamber;
 (b) a working and a counter electrode disposed within the sample chamber; and
 (c) a reagent composition disposed in the sample chamber, said reagent composition comprising (i) an active redox enzyme effective to oxidize the analyte, (ii) a mediator compound, and (iii) a shuttle compound, wherein
  when a sample containing analyte is introduced into the sample chamber, the redox enzyme oxidizes the analyte and produces an inactive enzyme that is reduced,
  the mediator is [Os(Mebpy)$_2$Pic]$^{+/2+}$ and
  the shuttle is ferri/ferrocyanide.
7. The sensor of claim 6, wherein the shuttle compound is present in at least a ten-fold excess with respect to the mediator compound on a molar basis.
8. The sensor of claim 6, wherein the reagent composition further comprises a third electron transfer agent that transfers electrons between the mediator and the shuttle.
9. The sensor of claim 6, wherein the analyte is glucose and the enzyme is glucose oxidase.

* * * * *